United States Patent
Bittenson (10) Patent No.: US 9,192,369 B2
(45) Date of Patent: Nov. 24, 2015

(54) STACKED PLATE SUTURE ANCHOR (75) Inventor: Steven N. Bittenson, Raynham, MA (US)

(73) Assignee: DePuy Mitek, LLC, Raynham, MA (US)

( * ) Notice: Subject to any disclaimer, the term of this patent is extended or adjusted under 35 U.S.C. 154(b) by 336 days.

(21) Appl. No.: 13/434,997

(22) Filed: Mar. 30, 2012

(65) Prior Publication Data
US 2013/0261663 A1  Oct. 3, 2013

(51) Int. Cl.
*A61B 17/04* (2006.01)

(52) U.S. Cl.
CPC ..... *A61B 17/0401* (2013.01); *A61B 2017/0409* (2013.01); *A61B 2017/0429* (2013.01); *A61B 2017/0446* (2013.01); *A61B 2017/0451* (2013.01); *A61B 2017/0459* (2013.01)

(58) Field of Classification Search
CPC .......... A61B 17/0401; A61B 2017/0409; A61B 2017/0459; A61B 2017/0446; A61B 2017/0451; A61B 2017/0429
USPC ......... 606/232, 213, 215, 216, 217, 218, 280, 606/70, 71, 902, 903, 904, 905, 906, 103; 411/340, 341, 343, 172, 173, 457; 24/712, 327, 136 R, 127, 115 G, 115 M, 24/712.9

See application file for complete search history.

(56) References Cited

U.S. PATENT DOCUMENTS

| 4,401,172 | A | | 8/1983 | Kessler | |
|---|---|---|---|---|---|
| 4,760,678 | A | | 8/1988 | Chambers | |
| 4,787,592 | A | * | 11/1988 | Aoshika | 248/327 |
| 4,899,743 | A | | 2/1990 | Nicholson | |
| 4,946,468 | A | | 8/1990 | Li | |
| 4,968,315 | A | | 11/1990 | Gatturna | |
| 5,002,550 | A | | 3/1991 | Li | |
| 5,024,666 | A | * | 6/1991 | Pituch | 604/263 |
| 5,207,679 | A | | 5/1993 | Li | |
| 5,217,486 | A | | 6/1993 | Rice | |
| 5,372,604 | A | | 12/1994 | Trott | |
| 5,411,522 | A | | 5/1995 | Trott | |
| 5,417,691 | A | * | 5/1995 | Hayhurst | 606/232 |
| 5,500,001 | A | | 3/1996 | Trott | |
| 5,501,683 | A | | 3/1996 | Trott | |
| 5,501,696 | A | | 3/1996 | Trott | |
| 5,505,735 | A | | 4/1996 | Li | |
| 5,522,845 | A | | 6/1996 | Wenstrom, Jr. | |
| 5,571,104 | A | | 11/1996 | Li | |
| 5,591,163 | A | | 1/1997 | Thompson | |
| 5,601,557 | A | | 2/1997 | Hayhurst | |
| 5,643,288 | A | | 7/1997 | Thompson | |
| 5,647,874 | A | | 7/1997 | Hayhurst | |
| 5,662,654 | A | | 9/1997 | Thompson | |
| 5,697,931 | A | | 12/1997 | Thompson | |
| 5,800,550 | A | * | 9/1998 | Sertich | 623/17.16 |

(Continued)

*Primary Examiner* — Elizabeth Houston
*Assistant Examiner* — Lucas Paez (57) ABSTRACT

A surgical anchor comprises a plurality of plates configured into a stack with successive plates within the stack being vertically arrayed with respect to the stack. The stack has an undeployed configuration, and a deployed configuration. In the deployed configuration one or more of the plates is positioned outwardly more laterally with respect to the stack than in the undeployed configuration so as to retain the anchor in a bone hole. A biasing member between the plates in the stack biases the one or more plates toward the deployed configuration. The biasing member can provide a torsional force to induce the plates to rotate and fan outwardly.

14 Claims, 9 Drawing Sheets

(56) References Cited

U.S. PATENT DOCUMENTS

| | | |
|---|---|---|
| 6,013,083 A | 1/2000 | Bennett |
| 6,042,583 A | 3/2000 | Thompson |
| 6,206,886 B1 | 3/2001 | Bennett |
| 6,547,800 B2 | 4/2003 | Foerster |
| 7,090,690 B2 | 8/2006 | Foerster |
| 7,238,188 B2 * | 7/2007 | Nesper et al. ............ 606/328 |
| 7,651,528 B2 | 1/2010 | Montgomery |
| 7,674,274 B2 | 3/2010 | Foerster |
| 7,766,939 B2 | 8/2010 | Yeung |
| 2003/0088252 A1 | 5/2003 | Kaikkonen |
| 2004/0138707 A1 | 7/2004 | Greenhalgh |
| 2006/0282081 A1 | 12/2006 | Fanton |
| 2006/0282082 A1 | 12/2006 | Fanton |
| 2006/0282083 A1 | 12/2006 | Fanton |
| 2007/0156148 A1 | 7/2007 | Fanton |
| 2007/0156149 A1 | 7/2007 | Fanton |
| 2007/0156150 A1 | 7/2007 | Fanton |
| 2007/0156176 A1 | 7/2007 | Fanton |
| 2007/0293866 A1 | 12/2007 | Stoeckel |
| 2008/0294204 A1 | 11/2008 | Chirico |
| 2013/0204297 A1 * | 8/2013 | Melsheimer et al. ...... 606/232 |

* cited by examiner

STACKED PLATE SUTURE ANCHOR

FIELD OF THE INVENTION

The invention relates generally to devices and methods for fixing an implant to body tissue and more particularly to anchors including knotless anchors for attaching implants, suture, or soft tissue to bone.

BACKGROUND

A common type of injury, especially among athletes, is the complete or partial detachment of soft tissue including tendons or ligaments from bone. Tissue detachment may occur during a fall, by overexertion, or for a variety of other reasons. Surgical intervention is often needed, particularly when tissue is completely detached from its associated bone. Currently available devices for mechanical tissue reattachment in these and other orthopedic repairs include screws, staples, tacks and suture anchors. Suture anchors generally have an anchoring body for establishing a firm connection to bone, and one or more suture-retaining feature such as an eyelet or other passage that facilitates connection to and positioning of the separated tissue, to effect its repair to the bone.

One objective in improving the outcome of surgical procedures to repair a tissue detachment is to minimize surgical trauma to the patient, that is, to minimize trauma caused by the surgical procedure and not associated with the original injury. Progress in this field in recent years has included the introduction of minimally invasive surgeries, including arthroscopic surgeries where, for example, an anchor loaded with suture and mounted on an inserter device can be passed to a surgical site and fixed to bone via a surgical cannula positioned through a small opening in the patient's skin, thereby minimizing the size of the associated surgical incision and associated trauma.

The design of the suture anchor itself, including how it is fixed in bone and how it retains suture, is very important to surgical outcome, as well as to reducing the difficulty of performing technically challenging arthroscopic procedures, where the surgeon is required to manipulate sutures, anchors, soft tissue and bone, using specialized tools that must be operated through the narrow diameter cannula. Tying knots at a surgical site that is accessed only through a cannula can be particularly challenging. Early suture anchor designs typically routed suture slidingly through an eyelet in the anchor body so the suture could be tied between the anchor and soft tissue using surgical knots, commonly after drawing the damaged tissue to the anchor in bone.

Some more recent anchors are configured to retain suture without using knots, either via a unidirectional suture passage through the anchor, or using a mechanism that actively clamps the suture to prevent suture sliding through the eyelet after completion of the repair. Although some knotless suture anchors have been developed and can somewhat simplify a surgeon's tasks in minimally invasive surgeries, it remains challenging to provide anchors with which soft tissue can be drawn to a desired location on bone independently of locking the anchor body itself into the bone.

Further, many current suture anchors and especially many knotless anchors require a substantial depth of penetration into the bone for fixing the anchor, the depth often greatly exceeding a diameter or other cross sectional dimension of the anchor. In some situations such anchors are longer in their direction of insertion into bone than would be optimal for patient safety, for example, in some shoulder and spinal surgeries where adequate depth for the anchor or an opening to receive the anchor within the bone may not be available or easily evaluated in advance by the surgeon.

Therefore there is a need for improved anchoring devices that provide knotless attachment of suture or soft tissue to bone, as well as suture anchors designed for minimum penetration into bone.

SUMMARY

A surgical anchor according to the present invention comprises a plurality of plates configured into a stack with successive plates within the stack being vertically arrayed with respect to the stack. The stack has an undeployed configuration, and a deployed configuration. In the deployed configuration one or more of the plates is positioned outwardly more laterally with respect to the stack than in the undeployed configuration. A biasing member between the plates in the stack biases those plates toward the deployed configuration.

Preferably, the biasing member connects the plates to each other. Preferably, adjacent plates in the stack have retention openings therethrough which are aligned with one another when the stack is in the undeployed configuration. An elongated deployment member positioned through the aligned retention openings retains the stack in the undeployed configuration against the bias and is removable from the anchor to reconfigure the anchor to the deployed configuration. In one aspect of the invention, the deployment member comprises an external screw thread and the aligned retention openings in the undeployed configuration comprise a corresponding internal screw thread.

Preferably, a suture opening is provided through at least one of the plates and receives at least one suture therethrough. In one aspect of the invention, suture openings go through each of at least two adjacent plates in the stack, with each such suture opening configured to receive at least one suture slidingly therethrough. The suture openings are aligned with one another when the stack is in the undeployed configuration. The suture openings are misaligned with one another when the stack is in the deployed configuration so as to then restrict sliding passage of suture through the suture openings. One or more of the suture openings can comprise a slot into its plate from an outside edge of the plate.

In one aspect of the invention, at least one of the one or more of the plurality of plates which are positioned outwardly more laterally with respect to the stack in the deployed configuration has an outside edge which is configured for either or gripping or cutting into tissue in the deployed configuration. For instance, the outside edge can be sharp for cutting into a wall of the opening in the material upon deployment of the anchoring member or it can be serrated for gripping a wall of the opening in the material upon deployment of the anchoring member.

Preferably, the biasing member comprises a torsion member, such as a portion of spring metal. The torsion member preferably biases the one or more plates to rotate about an axis. The biasing member can comprise a slot into one of the one or more plates from a radial edge thereof, allowing one portion of the plate to move with respect to the rest of the plate due to flexion of the plate at the slot.

Preferably, the stack has a maximum lateral dimension in its deployed configuration which exceeds the maximum lateral dimension in its undeployed configuration, the increase in lateral dimension providing holding into the bone hole. Also preferably, the stack has a lateral cross sectional area in its deployed configuration which exceeds the lateral cross sectional area in its undeployed configuration, the increase in cross sectional area providing holding into the bone hole.

A method according to the present invention provides for fastening soft tissue to a bone. The method comprises the steps of: preparing a bone hole in the bone for receiving a suture anchor having a length of suture connected thereto, the suture anchor comprising a plurality of plates configured into a stack, the stack having an undeployed configuration, and a deployed configuration in which one or more of the plates is positioned outwardly more laterally with respect to the stack than in the undeployed configuration, and a biasing member between the plates in the stack biasing the one or more plates toward the deployed configuration; positioning the suture anchor in the opening while the suture anchor is in the undeployed configuration; connecting the suture to the soft tissue; tensioning the suture to draw the soft tissue toward the bone; and deploying the anchor so that the biasing member moves the plates into the deployed configuration to retain the anchor in the bone hole.

Preferably, the method further includes the step of holding the suture anchor in the undeployed configuration via a retention member passed through the plates. The step of deploying the anchor then can comprise removing the retention member from the plates. In one aspect of the invention, the retention member is threaded into the plates and the step of removing the retention member comprises unthreading it from the plates.

Preferably, the suture passes through openings in registry with each other in adjacent plates when the suture anchor is in the undeployed configuration and the suture is locked relative to the suture anchor via movement of the openings out of registry with each other when the suture anchor is deployed into the deployed configuration.

BRIEF DESCRIPTION OF THE DRAWINGS

This invention is described with particularity in the appended claims. The above and further aspects of this invention may be better understood by referring to the following description in conjunction with the accompanying drawings, in which like numerals indicate like structural elements and features in various figures. The drawings are not necessarily to scale, emphasis instead being placed upon illustrating the principles of the invention.

DESCRIPTION

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

The present invention generally provides anchoring systems and methods for joining materials together using expandable anchoring devices, with particular application to surgical reapproximation of damaged soft tissue to a bone. In some embodiments, a length of suturing material between the soft tissue and the anchor can be adjusted to desirably configure the repair, then locked in place without tying knots.

An anchor according to the present invention has an anchor body comprising two or more plate-like components (plates) that can be planar disks or have another cross-sectional shape, stacked together to present a first effective transverse cross-section of the stack in an undeployed configuration. At least two of the plates in the stack are coupled to one another by a torsional spring element that is biased to rotate the plates with respect to one another substantially in their respective planes and about an effective axis of the torsional element extending between the coupled plates. Before deployment, the anchor is maintained in the undeployed configuration against the torsional spring bias, by a deployment member positioned through aligned openings through the plates of the stack. Removal of the deployment member from the openings releases the plates to reconfigure the stack in response to the torsional bias, to a larger effective cross-section comprising a deployed configuration.

The maximum geometric expansion of the anchor that is achievable on deployment is limited by the number and dimensions of the plates in the stack, the relative orientations of the plates in the deployed (torsionally relaxed) configuration, and the position of each torsional element with respect to the plates it couples in the stack, with more eccentrically positioned torsional elements generally providing more available expansion. For example, a two-plate stack having torsional elements coupling the plates together at a location near their respective edges and torsionally biased to deploy with a 180-degree rotation of the plates with respect to one another, could provide nearly a doubling of the maximum cross-sectional dimension between the undeployed and deployed configurations. A three-plate stack comprising diametrically opposed spring elements, each torsionally biased to deploy with a 180-degree rotation of the plates with respect to one another, could provide nearly a tripling of the maximum cross-sectional dimension from the undeployed configuration to the deployed configuration.

Figures 1A, 1B:
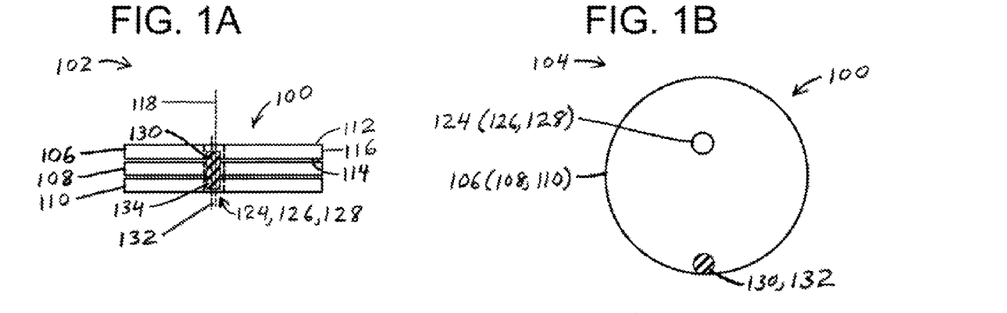
FIGS. 1A and 1B are, respectively, schematic side and top views of a first embodiment of an anchor body according to the present invention, in an undeployed configuration.

Referring more particularly to the figures, FIGS. 1A and 1B show a first embodiment of an anchor body 100 according to the present invention in a schematic side view 102 and top view 104, respectively, in an undeployed configuration. The anchor body 100 is seen to include a first 106, a second 108 and a third plate 110 arranged into a minimum transverse cross sectional area aligned stack. In the top view 104, only the first plate 106 is visible. Each plate, as shown for the first plate in FIG. 1A, has a respective upper surface 112, a lower surface 114 and a bounding outside edge 116 therebetween. The plates 106, 108, 110 are illustrated as having flat and mutually parallel upper and lower surfaces 112, 114, but various surface features and moderate surface curvature of the plates can be accommodated without deviating from the scope or intent of the invention. A common reference axis 118 substantially normal to the plate surfaces is shown positioned through the anchor body 100. For illustrative purposes, most anchor embodiments shown herein include three plates as shown in FIGS. 1A and 1B, but embodiments constructed with as few as two plates or with four or more plates are within the scope of the present invention.

Figures 1C, 1D:
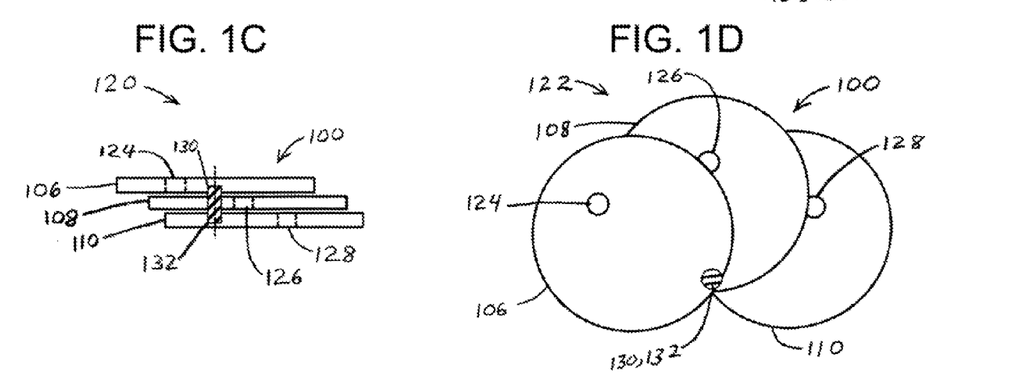
FIGS. 1C and 1D are, respectively, schematic side and top views of the anchor body of FIGS. 1A and 1B, in a deployed configuration.

FIGS. 1C and 1D are, respectively, a schematic side 120 and top view 122 of the anchor body 100 of FIGS. 1A and 1B, in a deployed configuration in which the plates 106, 108, 110 are seen to be misaligned with one another in the stack, presenting a larger cross sectional area in the deployed configuration 120, 122 than in the undeployed configuration 102, 104 shown in FIGS. 1A and 1B. This can be seen, for example, in the larger total area presented in the deployed top view 122 of FIG. 1D relative to the smaller total area presented in the undeployed top view 104 of FIG. 1B. Each of the first, second and third plates 106, 108, 110 is seen to have a respective retention opening 124, 126, 128 therethrough, the openings aligned along the reference axis 118 in the undeployed configuration 102, 104. The aligned openings 124, 126, 128 can reversibly receive a deployment member therethrough (not illustrated in FIGS. 1A-1D) for retaining the anchor body 100 in the undeployed configuration 102, 104 prior to deployment.

The first and second plates 106, 108 are coupled to one another by a first spring element 130 extending therebetween and providing a torsional spring bias about a torsional axis 132 parallel to the reference axis 118, toward the deployed configuration 120, 122 with respect to the first and second plates 106, 108. Similarly, the second and third plates 108, 110 are coupled to one another by a second spring element 134, the second spring element 134 providing a torsional spring bias about the torsional axis 132 toward the deployed configuration 120, 122 with respect to the second and third plates 108, 110. The torsional spring elements 130, 134 can comprise individual torsion springs, or, as illustrated in FIGS. 1A-1D, a single continuous spring element coupled among the plates 106, 108, 110. In various embodiments, adjacent (or nonadjacent) plates in the stack can be coupled by any of a variety of types of torsional spring constructions, several illustrative examples of which are shown herein below.

The spring elements 130, 134 are shown in FIGS. 1A-1D as positioned proximate to an edge of the anchor body 100, but in various other embodiments spring elements can be positioned away from the edges 116, at less eccentric locations of the respective plates 106, 108, 110. Positioning the spring elements further from an edge can enhance the structural stability of the anchor 100, at the expense of decreasing the geometric expansion achievable on anchor deployment.

The plates 106, 108, 110 are illustrated as having respective circular cross sections, for example, as seen in FIG. 1D, but other embodiments can include plates having any plate cross-sections or combinations of cross sections compatible with forming a stack that can be conveniently positioned into a corresponding preformed opening in a bone. In one embodiment, the cross-sectional shape of the anchor is polygonal. In another embodiment, the cross sectional shape is configured to resemble that of a natural footprint of a tendon or ligament attachment to a bone.

Figure 2A:
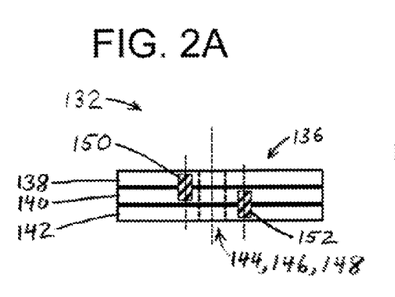
FIGS. 2A and 2B are, respectively, schematic side and top views of a second embodiment of an anchor body according to the present invention, in an undeployed configuration.
Figure 2B:
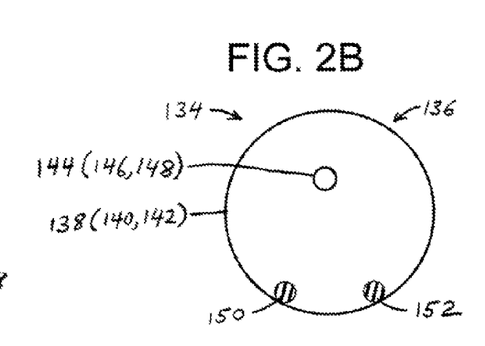

Now turning to FIGS. 2A through 4D, various other anchor body embodiments are illustrated. The embodiments of FIGS. 2A through 4D are described principally with reference to differences between each respective embodiment and the anchor body 100 associated with FIGS. 1A-1D. FIGS. 2A and 2B schematically show a side 132 and a top view 134 of a second embodiment of an anchor body 136 in an undeployed configuration. The anchor body 136 includes first, second and third plates 138, 140, 142 and having respective retention openings 144, 146, 148, similar to the plates of the first embodiment, but in the embodiment of FIGS. 2A and 2B, a first torsional spring element 150 coupling the first 138 and the second plate 140, and a second torsional spring element 152 coupling the second 140 and the third plate 142, are displaced circumferentially with respect to one another about the anchor body 136, with correspondingly displaced respective torsional axes 154, 156.

Figure 2C:
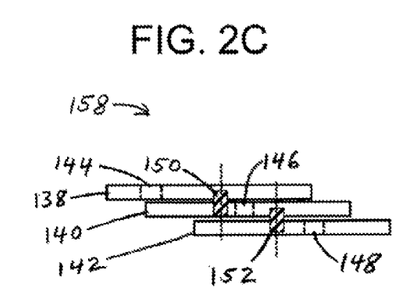
FIGS. 2C and 2D are, respectively, schematic side and top views of the anchor body of FIGS. 2A and 2A, in a deployed configuration.
Figure 2D:
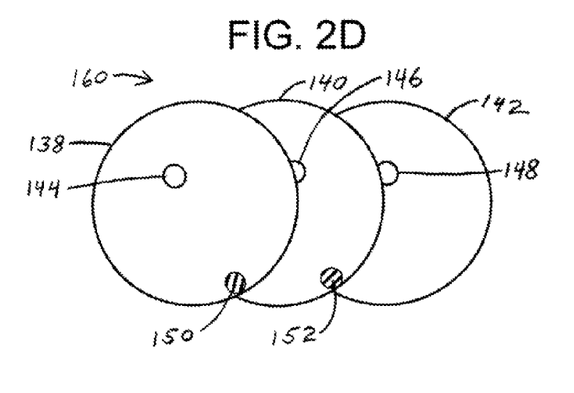

The circumferential displacement between the first torsional spring element 150 and the second torsional spring element 152 can comprise any separation along the circumferences of the respective plates, from closely adjacent to one another through diametrically opposed torsional spring elements. Each of the first 150 and the second torsion spring element 152 is biased toward an increased cross section deployed configuration shown schematically in FIG. 2C in a side view 158 and in FIG. 2D in a top view 160.

Figure 3A:
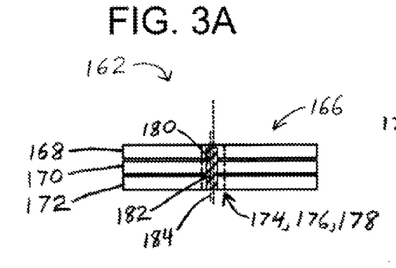
FIGS. 3A and 3B are, respectively, schematic side and top views of a third embodiment of an anchor body according to the present invention, in an undeployed configuration.
Figure 3B:
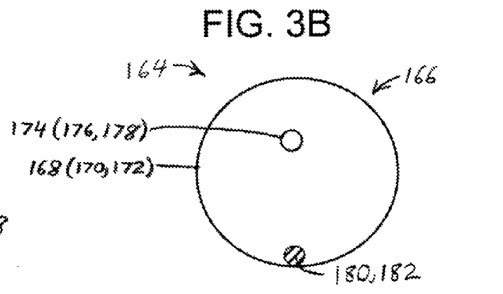
Figure 3C:
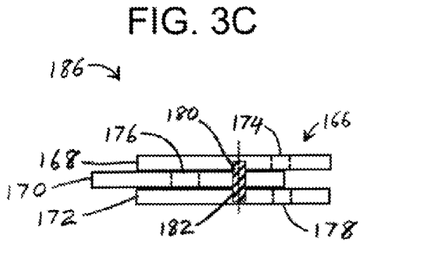
FIGS. 3C and 3D are, respectively, schematic side and top views of the anchor body of FIGS. 3A and 3B, in a deployed configuration.
Figure 3D:
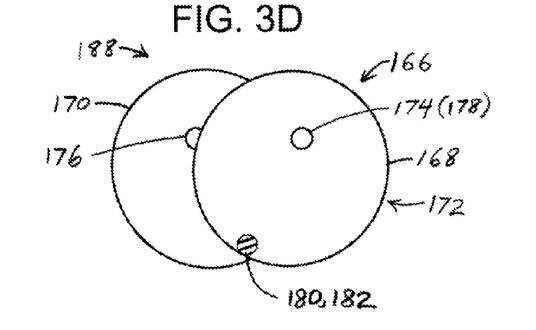

FIGS. 3A and 3B schematically show a side 162 and a top view 164 of a third embodiment of an anchor body 166 in an undeployed configuration. The anchor body 166 includes first, second and third plates 168, 170, 172, with corresponding retention openings 174, 176, 178, similar to the plates of the first and second embodiments, but in the embodiment of FIGS. 3A and 3B, a first torsional spring element 180 coupling the first 168 and the second plate 170, and a second torsional spring element 182 coupling the second 170 and the third plate 172, are oppositely biased (toward rotation in angularly opposite senses) with respect to one another, but sharing a common torsional axis 184. FIGS. 3C and 3D schematically show a respective side 186 and a top view 188 of the anchor body 166 of FIGS. 3A and 3B in a deployed configuration, illustrating the second plate 170 being displaced with respect to the first 168 and the third plate 172, which may remain substantially aligned with one another after deployment, illustrated as the third plate 172 being hidden by the first pate 168 in FIG. 3D.

Figure 4A:
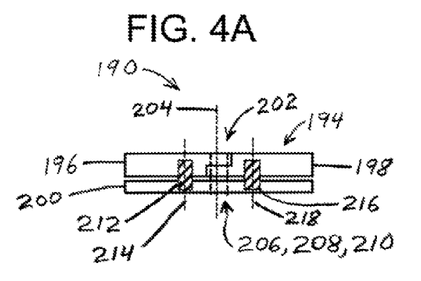
FIGS. 4A and 4B are, respectively, schematic side and top views of a fourth embodiment of an anchor body according to the present invention, in an undeployed configuration.
Figure 4B:
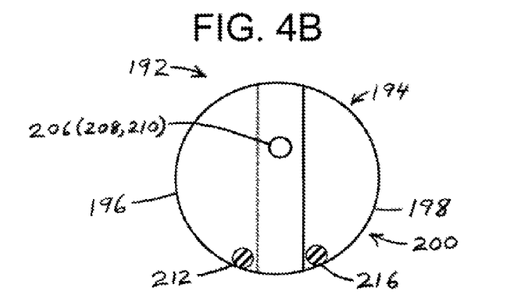
Figure 4C:
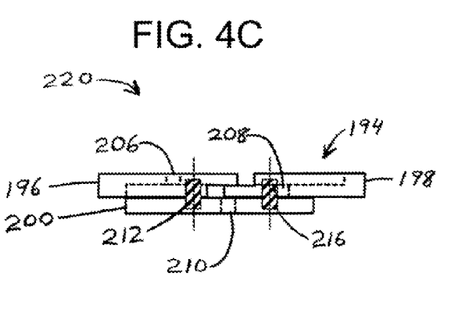
FIGS. 4C and 4D are, respectively, schematic side and top views of the anchor body of FIGS. 4A and 4B, in a deployed configuration.
Figure 4D:
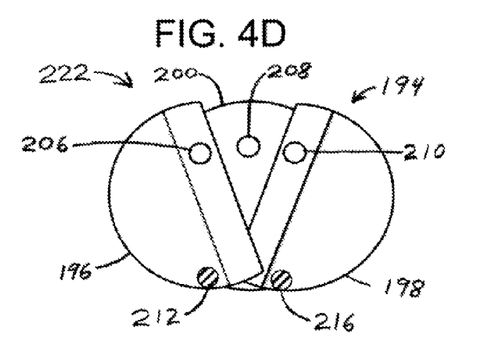

FIGS. 4A and 4B schematically show a side 190 and a top view 192 of a fourth embodiment of an anchor body 194 in an undeployed configuration. The anchor body 194 of the fourth embodiment includes first, second and third plates 196, 198, 200 where the first 196 and the second plate 198 individually only partially cover the third plate 200, the first 196 and the second plate 198 having a central region of overlap 202 over the third plate 200. A common reference axis 204 is seen to pass through all the plates in the anchor body 194, and along which are aligned retention openings 206, 208, 210 through each of the plates 196, 198, 200 respectively, for reversibly receiving a deployment member therethrough for retaining the anchor body in the undeployed configuration prior to deployment.

A first torsion spring element 212 couples the first 196 and the third plate 200 along a first torsional axis 214 and, circumferentially displaced from the first torsion spring element 212, a second torsion spring element 216 couples the second 198 and the third plate 200 along a second torsional axis 218. Each of the first 212 and the second torsion spring element 216 is biased toward an increased cross section deployed configuration shown schematically in FIG. 4C in a side view 220 and in FIG. 4D in a top view 222. The embodiments shown in FIGS. 1A-4D are illustrative only, and many other anchor bodies can be constructed according to the principles of the present invention.

Figure 5A:
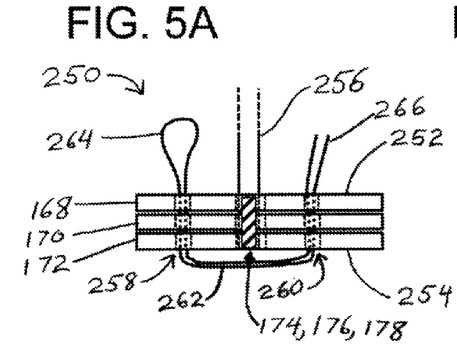
FIGS. 5A and 5B are schematic side views of a single-stage deployment suture anchor according to the present invention, in undeployed and deployed configurations, respectively.

FIG. 5A schematically shows a suture anchor 250 according to the present invention, in an undeployed configuration. The anchor has a proximal end 252 and a distal end 254. The anchor 250 is seen to comprise the anchor body 166 shown in FIGS. 3A-3D, but a suture anchor can be similarly constructed using any of the anchor embodiments shown in FIGS. 1A-4D, or other anchor bodies employing the principles of the present invention. A deployment member 256 is seen to be removably disposed in the anchor 250 through the retention openings 174, 176, 178 in the respective plates 168, 170, 172, to retain the anchor 250 in the undeployed configuration. In one embodiment, the deployment member 256 is slidingly disposed through the retention openings 174, 176, 178. In another embodiment, the deployment member 256 is externally screw-threaded and one or more of the retention openings 174, 176, 178 is correspondingly internally screw threaded for removably threading the deployment member 256 therethrough.

The anchor 250 is also seen to include a first 258 and a second set of suture openings 260 for slidingly receiving suture 262 through the plates 168, 170, 172, each set of suture openings being aligned therethrough in the undeployed configuration. In other embodiments, any number of sets of suture openings can be provided through the plates, consistent with the available surface area of the plates. In one embodiment, one set of suture openings is provided. In other embodiments, three or more sets of suture openings are provided.

In FIG. 5A, the suture 262 is seen to be threaded distally through the second set of suture openings 260 and again proximally through the first set of suture openings 258. In an embodiment, the suture 262 terminates in a suture loop 264 that can be used to draw tissue, another suture or another object toward the anchor 250 by tensioning the end 266 of the suture 262 opposite the loop 264 through the anchor 250.

Figure 5B:
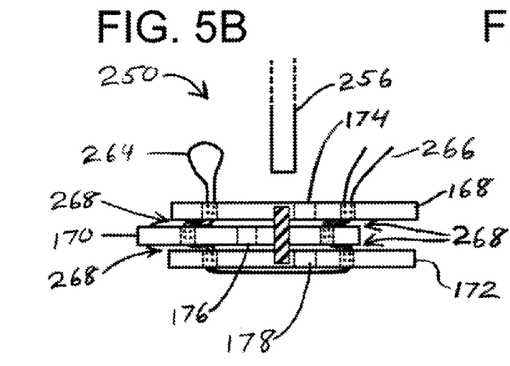

Now turning to FIG. 5B, the anchor 250 is shown in a deployed configuration wherein the deployment member 256 has been removed from the retention openings 174, 176, 178, freeing the plates 168, 170, 172 to adopt the deployed configuration in response to the torsional spring bias. In addition, deployment of the anchor 250 is seen to misalign the sets of suture openings 258, 260 among the plates 168, 170, 172, thereby causing interference between the suture and the plates at locations 268 along the suture within the anchor 250. The interference is operative to lock the suture 262 in the anchor 250, preventing further sliding of the suture 262 through the suture openings 258, 260.

Figure 6A:
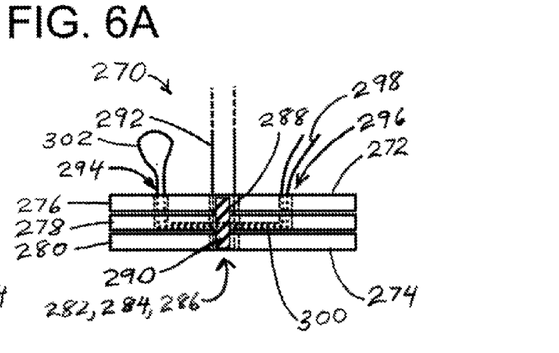
FIGS. 6A, 6B and 6C are schematic side views of a two-stage deployment suture anchor according to the present invention, in undeployed, intermediately deployed and fully deployed configurations, respectively.

FIG. 6A schematically shows in an undeployed configuration an embodiment of a suture anchor 270 constructed for two-stage deployment according to the present invention. The anchor 270 has a proximal end 272 and a distal end 274. The anchor 270 generally resembles the anchor 250 shown in FIG. 5A, differ with regard to the positioning of suture therethrough.

The anchor 270 is seen to comprise a first 276, a second 278 and a third plate 280, and respective retention openings 282, 284, 286 formed therethrough. A first torsional spring element 288 couples the first 276 and the second plate 278, and a second torsional spring element 290 couples the second 278 and the third plate 280, each spring element being torsionally biased toward a deployed configuration of the anchor 270. A deployment member 292 is seen to be removably disposed in the anchor 270 through the retention openings 282, 284, 286 in the respective plates 276, 278, 280, to retain the anchor 270 in the undeployed configuration. A first set 294 and a second set of suture openings 296 is provided for disposing suture 298 slidingly through the first 276 and the second plate 278, and an internal conduit 300, for example, a groove formed in the second plate 278, is also provided, for passing the suture 298 slidingly between the first 294 and the second set of suture openings 296 internally to the anchor 270, without mechanical interference with the third plate 280. The deployment member 292 is configured for stepwise removal from the anchor 270, for example via external screw threads on the deployment member 292 and mating internal screw threads on one or more of the retention openings 282, 284, 286.

In FIG. 6A, the suture 298 is seen to be threaded distally through the second set of suture openings 296, transversely along the internal conduit 300 and exiting proximally through the first set of suture openings 294. The suture 298 can comprise a suture loop 302 similarly configured to the suture loop 264 associated with the anchor 250 of FIGS. 5A and 5B.

Figure 6B:
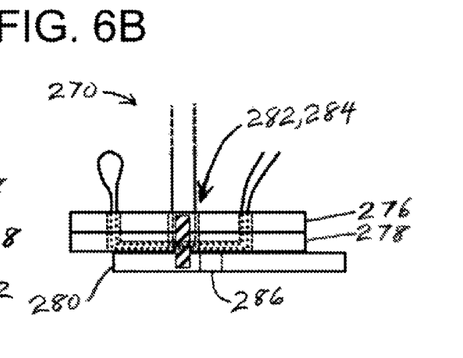

In a first stage of deployment illustrated schematically in FIG. 6B, the deployment member 292 is seen to have been partially removed from the anchor 270, for example by unthreading the deployment member 292 from the retention opening 286 in the third plate 280 while leaving it engaged with the respective retention openings 282, 284 in the first 276 and the second plate 278, thereby releasing the third plate 280 to move to a deployed configuration with respect to the second 278 and the first plate 276, under the bias of the second torsional spring element 290, while maintaining slidability of the suture 298 through the anchor 270.

Figure 6C:
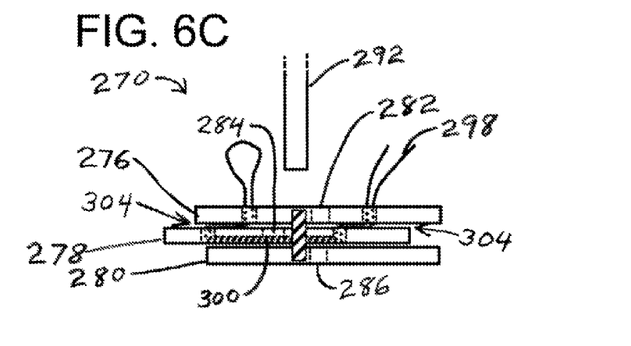

In a second stage of deployment illustrated in FIG. 6C, the deployment member 292 is fully removed from the anchor 270, completing deployment of the anchor 270 to a fully deployed configuration. The second stage of deployment of the anchor 270 is also seen to misalign the sets of suture openings 294, 296 between the first 276 and the second plate 278, thereby causing interference between the suture and the plates at locations 304 along the suture 298 within the anchor 270. The interference is operative to lock the suture 298 in the anchor 270, preventing further sliding of the suture 298 through the suture openings 294, 296 and the conduit 300.

In another embodiment, an anchor according to the present invention comprises two independent deployment members, each removably positioned through a respective retention opening in the anchor, removal of one of the deployment members operative to fix the anchor in bone, removal of the other deployment member operative to lock suture to the anchor.

In an embodiment of a method for using the suture anchor of FIGS. 6A-6C, the undeployed anchor 270 shown in FIG. 6A is positioned in an opening formed in a bone. The first stage of deployment shown in FIG. 6B fixes the anchor 270 in the opening in the bone against being pulled out of the bone while tension is applied to the suture 298 to draw tissue toward the anchor 270, and the second stage of deployment shown in FIG. 6C locks the suture 298 against further sliding through the anchor 270 while additionally fixing the anchor 270 into the opening in the bone.

Illustrative examples of several additional elements that can comprise anchors according to the present invention are shown in FIGS. 7A through FIG. 9. Any or combinations of these elements can be incorporated into various embodiments of the torsion-sprung anchors disclosed herein. Anchors according to the present invention expand in response to a spring bias when released to become fixed in bone. This fixation can be enhanced by the incorporation of edge features on plates comprising an anchor, to grip or cut into an interior wall of an opening of a substrate into which the anchor is to be deployed.

Figure 7A:
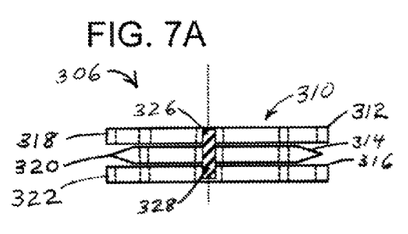
FIGS. 7A and 7B are, respectively, schematic side and top views of a suture anchor according to the present invention, illustrating exemplary embodiments of tissue-engaging edges on component plates of the anchor.
Figure 7B:
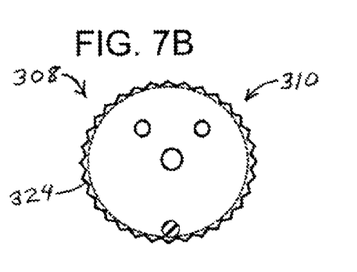

Turning to FIGS. 7A and 7B respectively, shown schematically in a side 306 and a top view 308 is an illustrative example of undeployed anchor 310 according to the present invention constructed from plates bearing edge features for enhancing fixation in bone upon expansion of the anchor 310 upon deployment. The anchor 310 is seen to comprise a first 312, a second 314 and a third plate 316, each having a respective circumferential edge 318, 320, 322. Each of the first 312 and the third plate 316 is seen to comprise edge features along its respective circumferential edge 318, 320 for gripping a wall of an opening in which the anchor 306 is to be deployed. In the embodiment illustrated in FIG. 7B, the edge features comprise circumferential serrations 324 about the first 318 and the third plate 322, but any edge features or edge materials for gripping the wall of the opening can be used with anchors according to the present invention.

The edge 320 of the second plate 314 is seen to be sharp for cutting into the wall of the opening upon deployment of the anchor 306 according to the present invention. The sharp-edged plate 320 is seen to be positioned between plates 318, 320 that do not having a sharp edge, thereby preventing the sharpened plate from penetrating into a wall of the opening until the anchor 306 expands on deployment in response to torsional bias associated with torsional spring elements 326, 328. Various combinations of fixation-enhancing edge features can be incorporated into anchor constructions according to the present invention.

Figure 8:
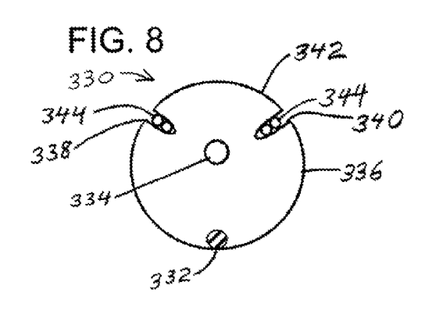
FIG. 8 is a schematic top view of a suture anchor having slots for receiving suture according to the present invention.

FIG. 8 is a schematic top view of a suture-slotted anchor 330 according to the present invention, in an undeployed configuration. The suture-slotted anchor 330 resembles other anchor embodiments hereinabove in that it comprises two or more plates coupled by one or more torsion spring element 332 biased toward an expanded, deployed configuration, and further comprising a retention opening 334 for receiving a deployment member. In the top view of FIG. 8, only a top plate 336 is visible. In the suture-slotted anchor 330, however, suture openings 338, 340 through the anchor 330 comprise slots extending inward from an edge 342 of the anchor, and into which suture 344 can be positioned laterally. Edge-slotted embodiments can be simpler for a surgeon to load with suture intraoperatively than embodiments wherein suture must be threaded through openings comprising holes bored or otherwise prepared through an anchor.

Figure 9:
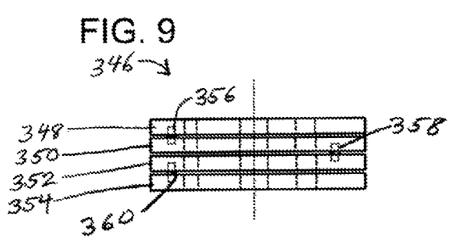
FIG. 9 is a schematic side view of a four-plate suture anchor according to the present invention.

FIG. 9 illustrates in a schematic side view, an anchor 346 according to the present invention constructed using four plates 348, 350, 352, 354 and an arrangement of diametrically opposed torsional spring elements 356, 358, 360 coupling adjacent plates in the anchor 346. Further, the torsional spring elements 356, 358, 360 are seen to be positioned radially inward from the respective plate edges. Positioning torsional spring elements inward from the anchor edge can enhance the stability of the anchor against out-of-plane motion of the plates upon anchor deployment.

Figure 10A:
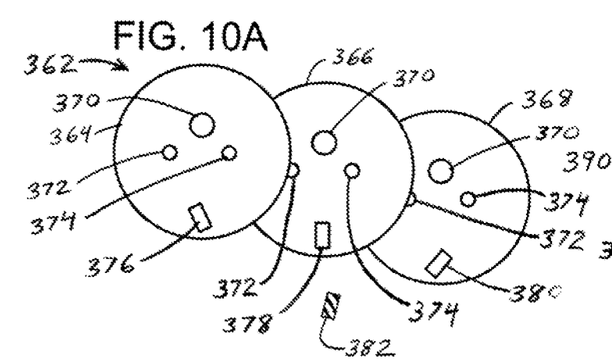
FIGS. 10A and 10B schematically illustrates means for establishing torsional biasing of an anchor according to the present invention incorporating a geometric cross section insert positioned through the anchor body.

The construction of expandable, torsionally biased anchors according to the present invention can be accomplished by a variety of means, several nonlimiting examples of which are schematically illustrated in FIGS. 10A through 12F. FIG. 10A schematically shows in a top view, anchor components 362 for constructing an embodiment of a torsionally sprung anchor. The components 362 include a first 364, a second 366 and a third plate 368 each plate having a respective retaining opening 370, and suture openings 372, 374, each opening configured to be aligned with respective openings in the other plates when stacked together into an anchor in an undeployed configuration.

Further, each of the plates 364, 366, 368 is seen to comprise a respective spring opening 376, 378, 380 therethrough and having a noncircular cross-sectional shape (illustrated as rectangular in FIG. 10A) for receiving a torsion bar 382 having an external cross sectional shape configured to be matingly received through the noncircular opening in each respective plate. The torsion bar 382 is also schematically illustrated in a perspective view in FIG. 10B. In each of the plates 364, 366, 368, the orientation of the noncircular shape of the respective spring opening is rotated about its own center with respect to the corresponding opening in an adjacent plate.

To assemble an anchor from the anchor components 362, the plates 364, 366, 368 are oriented with respect to one another so that the torsion bar 382 can be positioned through the respective spring openings 376, 378, 380. This orientation comprises a deployed anchor configuration. An external clamping force is then used to apply torsion to the torsion bar 382 among the plates to force the anchor into an aligned stack comprising an undeployed configuration analogous to the undeployed configuration in any of the embodiments disclosed hereinabove, in which a deployment member can be positioned through the respective retaining openings of the plates 364, 366, 368 to complete the assembly. The resulting anchor body comprises a torsional bias toward the deployed configuration, retained by the deployment member in the undeployed configuration. In an embodiment, the torsion bar is secured to one or more of the plates by welding or by another securing method.

Figure 11:
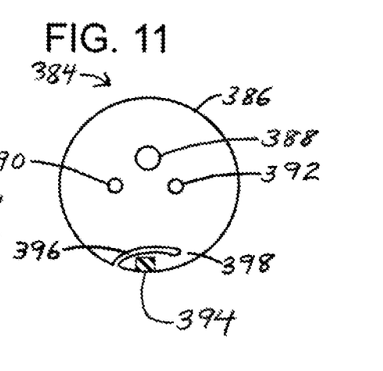
FIG. 11 is a schematic top view of an embodiment of an anchor according to the present invention wherein a torsional bias comprises a slot in one or more component plate of the anchor.

Now turning to FIG. 11, another means for providing torsional springing among plates comprising an anchor 384 according to the present invention is shown in a schematic top view, with only a top plate 386 of the anchor 384 being visible in FIG. 11. A retention opening 388 and suture openings 390, 392 are seen to be formed in the top plate 386. A rigid connection 394 couples the top plate 386 to an adjacent plate therebelow (not visible in FIG. 11). The top plate 386 is seen to include a slot 396 formed therethrough and configured so that resilience in a narrow portion 398 of the top plate 386 adjacent the slot 396 provides a torsional bias toward a deployed, expanded configuration of the anchor.

Anchors according to the present invention can be constructed using various materials and combinations of materials that can be formed into relatively rigid plates coupled together so that the anchor comprises torsional resilience among two or more plates. Materials of construction can include stainless steel or other biocompatible metals, and superelastic materials such as nickel-titanium alloys. In some embodiments the plates are formed as rigid members, and coupling elements therebetween comprise resilient members. In other embodiments the plates are constructed from a resilient material into which spring members are formed. In yet other embodiments a single resilient material is used to construct the entire anchor, with torsional resilience for coupling between plates being derived from relatively small cross section portions formed into the anchor.

In an embodiment, an anchor is formed substantially from a single piece of one of a spring steel alloy and a superelastic alloy. In a further embodiment the superelastic alloy comprises nickel and titanium. In another embodiment, an anchor comprises a plurality of plates formed from a relatively rigid surgically steel or stainless steel, and coupling elements therebetween comprise one of spring steel and a superelastic alloy. In yet another embodiment where respective resilient members are formed into the structure one or more plate of an anchor, for example as illustrated in FIG. 11, the plates are formed of a relatively elastic or superelastic material and coupling among the plates can comprise one or more substantially rigid element. Further, the anchors can be at least partially bioabsorbable, for example comprising bioabsorbable polymeric, bioceramic or bioerodable metallic or alloy plates coupled to one another by spring members formed therein and therebetween. In an embodiment, one or more plate comprises magnesium. In another embodiment, an anchor comprises stacked bioabsorbable plates and superelastic metallic wire formed therein as torsional members.

Figure 10B:
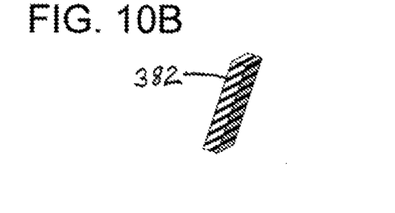
Figure 12A:
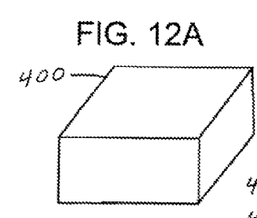
FIGS. 12A-12F schematically illustrate a method for fabricating a monolithic anchor according to the present invention.
Figure 12B:
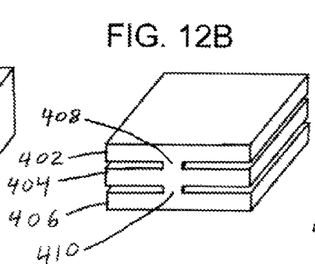

Anchors according to the present invention can be assembled using mechanically locked components as described hereinabove in association with FIGS. 10A and 10B, welded or otherwise fastened together, or including torsion elements integrally formed with plates as shown in FIG. 11. An illustrative example of a method for constructing an anchor as a unitary body according to the present invention is illustrated schematically in FIGS. 12A through 12F. Starting with FIG. 12A, a solid block 400 of a material having elastic properties, for example, a superelastic alloy, is seen in FIG. 12B to have been machined or otherwise shaped to form individual plates 402, 404, 406 coupled by relatively small cross-section members 408, 410 that are dimensioned to comprise torsionally resilient elements between adjacent ones of the plates.

Figure 12C:
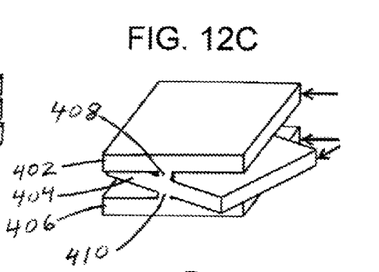
Figure 12D:
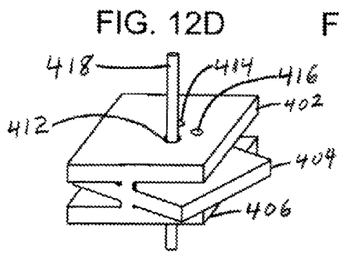

Now turning to FIG. 12C, torsional forces (represented by arrows in the figure) are externally applied and maintained to set a torsional bias among the plates 402, 404, 406, at the small cross-section members 408, 410. The torsional forces can be applied using any known clamping or other force-applying means. As seen in FIG. 12D, while maintaining the torsional bias among the plates 402, 404, 406, a retention opening 412 and one or more suture opening 414, 416 is formed through the anchor 400, that is, through all of the plates 402, 404, 406, and a deployment member 418 is positioned through the retention opening 412 to maintain the torsional bias upon removal of the externally applied forces.

Figures 12E, 12F:
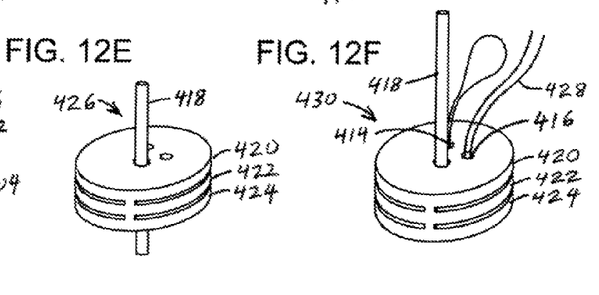

Now turning to FIG. 12E, the plates 402, 404, 406 are seen to have been machined or otherwise shaped together to form a minimum cross-sectional area stack of reshaped plates 420, 422, 424 comprising an anchor body 426, maintained by the deployment member 418 in an undeployed configuration against the torsional bias. Finally, as shown in FIG. 12F, suture 428 is positioned through the one or more suture opening 414, 416 to complete the construction of a suture anchor 430.

Anchors according to the present invention are applicable to many orthopedic surgical repairs and other procedures comprising the coupling of an object to bone, either in open or arthroscopic surgeries. FIGS. 13A through 13E illustrate an exemplary embodiment of a method for using an anchor according to the present invention to attach suture to bone. FIGS. 13A through 13E illustrate a procedure using the anchor 270 embodiment illustrated in FIGS. 6A through 6C, but the same principles apply for any anchor disclosed herein and variations thereof.

Figure 13A:
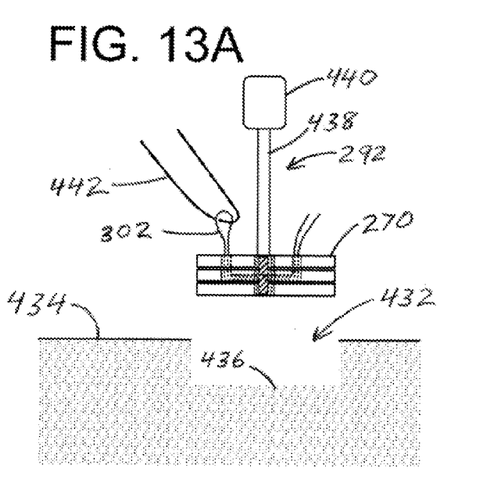
FIGS. 13A-13E schematically illustrate an example of a method for attaching suture to bone using a suture anchor according to the present invention.

Starting with FIG. 13A, an opening 432 is prepared in a bone 434 for receiving the anchor 270. The opening 432 can have a flat bottom 436 and requires a depth of penetration of the opening 432 into the bone 434 no greater than is needed to desirably seat the anchor 270. The deployment member 292 is seen to include a shaft 438 and a handle 440 that are dimensioned appropriately for a desired mode of anchor delivery, for example, the shaft 438 can be configured to be long enough to pass the anchor 270 through an arthroscopic cannula (not illustrated) to the opening 432 in the bone 434. In an embodiment, the deployment member 292 further comprises suture management means such as suture guides or retainers for simplifying delivery of the anchor 270 to a surgical site.

Figure 13B:
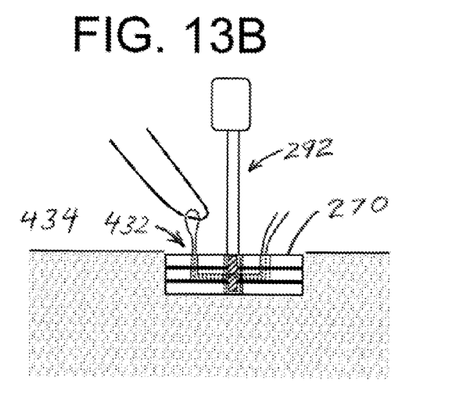
Figure 13C:
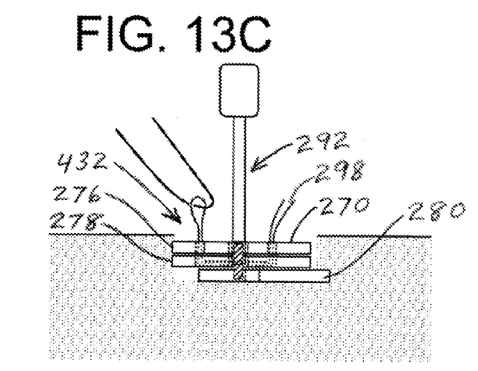

The suture loop 302 is seen to be connected to an attachment article 442 that can be another suture, a portion of detached tissue for repair to the bone 434, or another type of implant for retention to the bone 434. Turning to FIG. 13B, the anchor 270 is positioned in the opening 232 in the bone 234 in a desired location and orientation using the deployment member 292. Now turning to FIG. 13C, the anchor 270 is next partially deployed in a first deployment stage (corresponding to the deployment of the anchor 270 shown in FIG. 6B) by partially retracting the deployment member 292 proximally to release the third plate 280 toward its deployed configuration with respect to the first 276 and the second plate 278, thereby fixing the anchor 270 in the opening 432, while leaving the suture 298 slidingly disposed through the first 276 and the second plate 278.

Figure 13D:
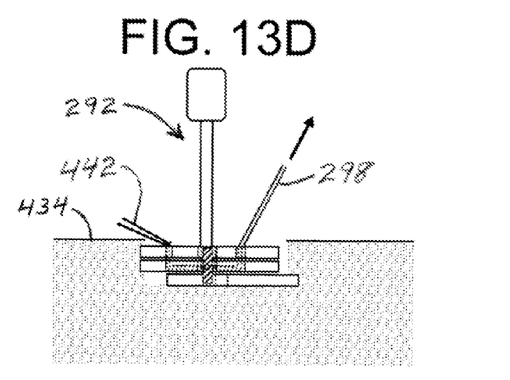
Figure 13E:
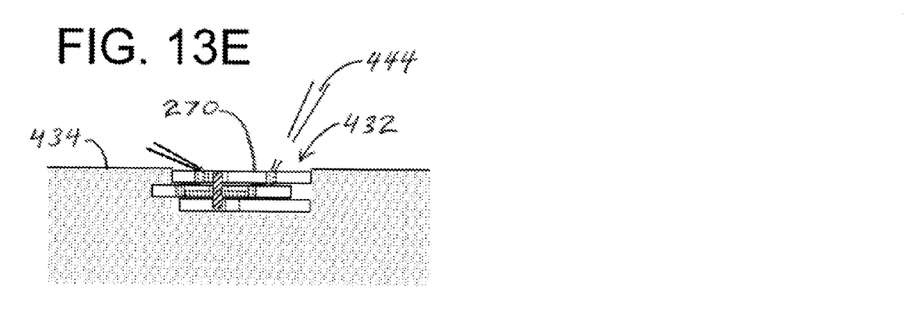

FIG. 13D illustrates a tensioning step wherein the suture 298 is tensioned to draw the attachment article 442 to the anchor 270, for example, thereby drawing a tendon or ligament connected thereto to the bone 434. To secure the repair, as shown in FIG. 13E, the deployment member 292 is completely withdrawn from the anchor 270 (second deployment stage), locking the suture 298 against further sliding through the anchor 270 and fully deploying the anchor in the opening 432 for final fixation to the bone 434. Finally, excess suture 444 can be trimmed from the anchor 270 to complete the repair.

Embodiments of the inventive anchors have been disclosed hereinabove generally for performing orthopedic surgical repairs employing sutures positioned through openings formed in the anchors, but the anchors comprising stacked, torsional spring-coupled plates can be applied in other types of procedures. In an embodiment, an undeployed anchor body according to the present invention is positioned in an opening in bone alongside damaged connective tissue that is also positioned in the opening, the opening being sized to accept both the anchor and the tissue. Deployment of the anchor alongside the soft tissue in the opening is operative to expand the anchor to trap and fix the connective tissue in the opening. Fasteners according to the present invention can also be applied in nonsurgical environments where an expandable anchor having a shallow penetration depth into a substrate is desired.

Advantageously, suture anchors according to the present invention provide knotless fixation of suture to bone. Further, fixing the anchor to the bone and locking the suture from further sliding through a passage in the anchor can be performed independently of one another. A surgeon is thus enabled to accurately control the tension applied to draw tissue or another implant to the bone before locking the suture against sliding with respect to the repair. The anchor fixation comprises components of the anchor moving laterally with respect to one another within a bone hole in response to torsional biasing of the components with respect to one another, to desirably provide expansion of the anchor perpendicular to its direction of insertion into an opening in bone, thereby providing little or no longitudinal play of the anchor in the opening during deployment.

Further, the lateral expansion achievable by deployment of the inventive anchors can advantageously provide large expansions in a cross-section dimension and effective area of the anchor relative to its undeployed cross section, for strong fixation in bone. The geometry of an anchor according to the present invention can, depending on its detailed design, enable expansion on deployment to several times an undeployed cross-section. Large expansion on deployment is achievable, for example, using an anchor comprising torsion elements diametrically opposed to one another among three plates in an undeployed configuration, and the anchor being torsionally biased for 180 degree rotation of each plate with respect to an adjacent plate.

Also advantageously, anchors according to the present invention can be implanted and fixed into a shallow opening in bone relative to a cross-sectional dimension of the anchor, providing secure fixation at surgical locations in the body where deeper drilling into bone is inconvenient for the surgeon or unsafe for the patient. By way of nonlimiting example, an inventive suture anchor having plate diameters of five millimeters and comprising a stack of three plates, each having a plate thickness of one millimeter and spaced not more than a half millimeter apart in the stack, would have an overall length of approximately four millimeters along its insertion direction, and requiring a similarly dimensioned preformed opening in the bone for deployment.

While the invention has been particularly shown and described with reference to specific preferred embodiments, it should be understood by those skilled in the art that various changes in form and detail may be made therein without departing from the spirit and scope of the invention as defined by the appended claims.

What is claimed is:

1. A surgical anchor comprising a plurality of plates configured into a stack with successive plates within the stack being vertically arrayed with respect to the stack;
   the stack having an undeployed configuration, and a deployed configuration in which one or more of the plates is positioned outwardly more laterally with respect to the stack than in the undeployed configuration;
   a biasing member between the plates in the stack biasing the one or more plates toward the deployed configuration;
   the stack having a first maximum lateral dimension in its deployed configuration which exceeds a second maximum lateral dimension in its undeployed configuration;
   retention openings through adjacent plates in the stack, the respective retention openings aligned with one another when the stack is in the undeployed configuration; and
   an elongated deployment member positioned through the aligned retention openings, the stack being retained by the deployment member in the undeployed configuration against the bias, the deployment member being removable from the anchor to reconfigure the anchor to the deployed configuration.

2. The surgical anchor of claim 1 in which the biasing member connects the plates to each other.

3. The surgical anchor of claim 1 wherein the deployment member comprises an external screw thread and the aligned retention openings in the undeployed configuration comprise a corresponding internal screw thread.

4. The surgical anchor of claim 1 and further comprising a suture opening through at least one of the plates and at least one suture therethrough.

5. The surgical anchor of claim 1 and further comprising suture openings through each of at least two adjacent plates in the stack, each suture opening configured to receive at least one suture slidingly therethrough, the suture openings being aligned with one another when the stack is in the undeployed configuration, and the suture openings being misaligned with one another when the stack is in the deployed configuration so as to restrict sliding passage of suture through the suture openings.

6. The surgical anchor of claim 1 wherein at least one of the one or more of the plurality of plates which are positioned outwardly more laterally with respect to the stack in the deployed configuration has an outside edge and wherein that outside edge is configured for at least one of gripping and cutting into tissue in the deployed configuration.

7. The surgical anchor of claim 6 wherein the outside edge is sharp for cutting into a wall of the bone hole in the material upon deployment of the anchoring member.

8. The surgical anchor of claim 6 wherein the outside edge is serrated for gripping a wall of the bone hole in the material upon deployment of the anchoring member.

9. The surgical anchor of claim 1 wherein the biasing member comprises a torsion member.

10. The surgical anchor member of claim 9 wherein the torsion member comprises a spring metal.

11. The surgical anchor of claim 9 wherein the torsion member biases the one or more plates to rotate about an axis.

12. The surgical anchor of claim 1 wherein the biasing member comprises a slot into one of the one or more plates from a radial edge thereof.

13. The surgical anchor of claim 1 wherein the stack has a first lateral cross sectional area in its deployed configuration which exceeds a second lateral cross sectional area in its undeployed configuration.

14. A surgical anchor comprising a plurality of plates configured into a stack with successive plates within the stack being vertically arrayed with respect to the stack;
   the stack having an undeployed configuration, and a deployed configuration in which one or more of the plates is positioned outwardly more laterally with respect to the stack than in the undeployed configuration;
   a biasing member between the plates in the stack biasing the one or more plates toward the deployed configuration;
   the stack having a first maximum lateral dimension in its deployed configuration which exceeds a second maximum lateral dimension in its undeployed configuration;

suture openings through each of at least two adjacent plates in the stack, each suture opening configured to receive at least one suture slidingly therethrough, the suture openings being aligned with one another when the stack is in the undeployed configuration, and the suture openings being misaligned with one another when the stack is in the deployed configuration so as to restrict sliding passage of suture through the suture openings; and wherein the suture openings comprise a slot in the at least one of the plates, the at least one of the plates having an outside edge and the slot extending into the plate from the outside edge.

* * * * *